(12) United States Patent
Todokoro et al.

(10) Patent No.: US 8,735,352 B2
(45) Date of Patent: May 27, 2014

(54) ADSORBENT FOR BLOOD COAGULATION FACTOR OR CELL ADHESION FACTOR AND METHOD FOR PURIFYING THE FACTOR

(71) Applicant: JNC Corporation, Tokyo (JP)

(72) Inventors: Masami Todokoro, Kanagawa (JP); Akiko Shimatani, Kanagawa (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 13/705,173

(22) Filed: Dec. 5, 2012

(65) Prior Publication Data

US 2013/0144039 A1 Jun. 6, 2013

(30) Foreign Application Priority Data

Dec. 5, 2011 (JP) ................................ 2011-265564

(51) Int. Cl.
*A61K 38/00* (2006.01)

(52) U.S. Cl.
USPC ........................................................ 514/13.5

(58) Field of Classification Search
USPC .................... 424/423; 514/7.1, 13.5; 530/350
See application file for complete search history.

(56) References Cited

U.S. PATENT DOCUMENTS 8,076,294 B2 * 12/2011 Kinney et al. ................. 514/17.2
2010/0022755 A1 1/2010 Umeda et al.

FOREIGN PATENT DOCUMENTS

WO 2008/075589 6/2008

OTHER PUBLICATIONS

GE Healthcare, "Affinity Chromatography Principles and Methods", Handbook from GE Healthcare, 1988, p. 69.
Takaki Koide, "Biochemical research by using of the collagen like triple helix peptide", with English abstract thereof, The Journal of Biochemistry, vol. 82, No. 6, Jun. 2010, p. 474-483.
Gloria A. Di Lullo et al., "Mapping the Ligand-binding Sites and Disease-associated Mutations on the Most Abundant Protein in the Human, Type I Collagen", The Journal of Biological Chemistry, vol. 277, No. 6, Feb. 8, 2002, p. 4223-4231.
Osamu Inoue et al., "Novel synthetic collagen fibers, poly(PHG), stimulate platelet aggregation through glycoprotein VI," Febs Letters, vol. 583, Jan. 5, 2009, p. 81-87.

* cited by examiner

*Primary Examiner* — Maryam Monshipouri
(74) *Attorney, Agent, or Firm* — Jianq Chyun IP Office

(57) ABSTRACT

An objective of the invention is to provide an adsorbent allowing purification of a blood coagulation factor or a cell adhesion factor under mild conditions, according to simple procedures, and at a low cost and safely while having a high affinity and a high resistance to deterioration, and a method for purifying the blood coagulation factor or the cell adhesion factor; a solution is to apply a polypeptide having peptide fragments represented by formula (1) as the adsorbent for the blood coagulation factor or the cell adhesion factor, and to purify the blood coagulation factor or the cell adhesion factor using the adsorbent:

$$-(Pro\text{-}Hyp\text{-}Gly)_n\text{-}$$

Wherein, in formula (1), n is an integer from 2 to 9,000.

5 Claims, No Drawings

ADSORBENT FOR BLOOD COAGULATION FACTOR OR CELL ADHESION FACTOR AND METHOD FOR PURIFYING THE FACTOR

CROSS-REFERENCE TO RELATED APPLICATIONS

This application claims the priority benefit of Japan application serial no. 2011-265564, filed on Dec. 5, 2011. The entirety of the above-mentioned patent application is hereby incorporated by reference herein and made a part of this specification.

TECHNICAL FIELD

The present invention relates to an adsorbent for a blood coagulation factor or a cell adhesion factor and a method for purifying the factor.

BACKGROUND ART

Chromatography is generally known as a method for purifying biomolecules such as a protein. Specific examples include cation exchange chromatography, anion exchange chromatography, gel filtration chromatography, hydrophobic interaction chromatography and affinity chromatography. An object protein can be highly purified by combining the processes. Therefore, the chromatography is an important technology in purification of erythropoietin, immunoglobulin or the like, to be used as a biomedicine, contained in blood, plasma or a culture liquid for a cell, for example. In particular, the affinity chromatography has a very higher selectivity to an object substance, as compared with other processes. Therefore, the object substance can be highly purified by a single operation, and the affinity chromatography is important as a technology by which a high productivity can be obtained in a short period of time of operation.

The affinity chromatography is performed by utilizing a ligand having an interaction with the object substance, and purification using the protein as the ligand may be performed. For example, an art is known in which an therapeutic antibodies is produced by purifying the immunoglobulins by using a protein A immobilized adsorbent, or a blood component such as fibronectin is purified by using a gelatin immobilized adsorbent.

The affinity chromatography using the protein as the ligand allows an efficient purification with a high selectivity. However, the affinity chromatography has a problem of degeneration or degradation of the ligand by alkaline washing, degradation of the ligand by protease, or deterioration of the ligand caused by weakness of the ligand per se.

Moreover, in the affinity chromatography using the protein as the ligand, an animal origin material may be mixed in a ligand material, and the affinity chromatography also has a problem of safety thereof. More specifically, a demand has been recently provided for avoiding use of a bovine origin gelatin as the ligand from a concern to zoonosis such as Bovine Spongiform Encephalopathy, and a ligand material in place of the animal origin material is required.

Furthermore, in the affinity chromatography using the protein as the ligand, conditions for recovering the object substance do not always become mild in consequence of a high affinity between the ligand and the object substance. For example, in one case, acidic conditions (pH 3, for example) are needed when allowing elution of the immunoglobulin from the protein A immobilized gel, and in another case, 8 M urea, 1 M NaBr, arginine or the like is used when allowing elution of the fibronectin from the gelatin immobilized gel (Non-patent literature No. 1). Under such severe elution conditions, the affinity chromatography has a fear of degeneration of the protein as the object substance, and expensiveness due to a high concentration of a reagent such as urea or arginine to be used for elution, and has a problem of cost and complicatedness thereof from necessity of treatment such as neutralization after an elution step.

Thus, an affinity ligand is required by which the protein can be purified in the purification of the protein under mild conditions, according to simple procedures, and at a low cost and safely while having a high affinity with the object substance and a high resistance to deterioration.

Meanwhile, a collagen well known as one of the biomolecules is a generic term for a protein having a triple helical structure formed of assembled three helices of polypeptides including repetitions of Gly-X-Y (wherein, X and Y represent various kinds of amino acids, X is Pro and Y is Hyp in many cases) in an identical direction.

A native collagen is known to be bonded with various kinds of biomolecules, or to have platelet aggregation capacity. A molecule such as a specific protein has been found to be bonded to a specific amino acid sequence in the native collagen so far (Non-patent literature No. 3). A study has been conducted for creating a collagen-like peptide to be bonded with a specific object molecule by utilizing such a finding. For example, a collagen-like peptide having a specific amino acid sequence to be bonded with collagen-binding molecules such as a von Willebrand factor is disclosed (Non-patent literature No. 2).

Moreover, a polypeptide having a repetition structure of a sequence of Pro-X-Gly (wherein X represents Pro or Hyp) as created as the collagen-like peptide has been found. The polypeptide has been found to have the platelet aggregation capacity (Non-patent literature No. 4), and a platelet aggregation induction substance containing the peptide has been disclosed (Patent literature No. 1). However, polypeptide fragments having the repetition structure of the sequence have not been known to be bonded with the fibronectin, the von Willebrand factor or the like with a high affinity.

CITATION LIST

Patent Literature

Patent literature No. 1: WO 2008/075589 A.

Non-Patent Literature

Non-patent literature No. 1: Affinity Chromatography Principles and Methods (Handbook from GE Healthcare) p. 69.

Non-patent literature No. 2: The Journal of Biochemistry, Vol. 82, No. 6, pp. 474-483, 2010.

Non-patent literature No. 3: THE JOURNAL OF BIOLOGICAL CHEMISTRY Vol. 277, No. 6, Issue of February 8, pp. 4223-4231, 2002.

Non-patent literature No. 4: FEBS Letters 583 (2009) 81-87.

SUMMARY OF INVENTION

Technical Problem

In view of the situation described above, an objective of the invention is to provide an adsorbent allowing purification of a blood coagulation factor or a cell adhesion factor under mild conditions, according to simple procedures, and at a low cost and safely while having a high affinity with an object substance and a high resistance to deterioration, and a method for purifying the blood coagulation factor or the cell adhesion factor.

Solution to Problem

The present inventors have diligently continued to conduct research for solving the problem, as a result, have found that a blood coagulation factor, a cell adhesion factor or the like is adsorbed on a polypeptide having peptide fragments including a repetition structure of a sequence of Pro-Hyp-Gly with a high affinity, and furthermore, is desorbed by a mild process for increasing a salt concentration.

The invention concerns an adsorbent for a blood coagulation factor or a cell adhesion factor, containing a polypeptide having peptide fragments represented by formula (1):

$$-(\text{Pro-Hyp-Gly})_n- \quad (1)$$

wherein n is an integer from 2 to 9,000.

The invention also concerns a solid phase carrier, immobilizing the adsorbent.

The invention further concerns a method for purifying a blood coagulation factor or a cell adhesion factor in a sample solution, including an adsorption step for bringing the sample solution into contact with the adsorbent or the solid phase carrier to adsorb the blood coagulation factor or the cell adhesion factor on the adsorbent.

More specifically, the invention is as described below.

Item 1. An adsorbent for a blood coagulation factor or a cell adhesion factor, containing a polypeptide having peptide fragments represented by formula (1) (hereinafter, described as an adsorbent of the invention):

$$-(\text{Pro-Hyp-Gly})_n- \quad (1)$$

wherein n is an integer from 2 to 9,000.

Item 2. The adsorbent according to item 1, wherein the blood coagulation factor or the cell adhesion factor is selected from the group consisting of a von Willebrand factor, fibronectin, glycoprotein VI (GPVI), integrin, heat shock protein 47, and vitronectin.

Item 3. The adsorbent according to item 1 or 2, wherein a weight average molecular weight of the polypeptide is in the range of 570 to 7,000,000.

Item 4. A solid phase carrier, immobilizing the adsorbent according to any one of items 1 to 3.

Item 5. A method for purifying a blood coagulation factor or a cell adhesion factor in a sample solution, including an adsorption step for bringing the sample solution into contact with the adsorbent according to any one of items 1 to 3, or the solid phase carrier according to item 4 to adsorb the blood coagulation factor or the cell adhesion factor on the adsorbent (hereinafter, described as a purification method of the invention).

Item 6. The method according to item 5, further including an elution step for bringing an eluting agent-containing eluate into contact the adsorbent or the solid phase carrier after the adsorption step to elute the blood coagulation factor or the cell adhesion factor.

Item 7. The method according to item 5 or 6, wherein the blood coagulation factor or the cell adhesion factor is selected from the group consisting of a von Willebrand factor, fibronectin, glycoprotein VI (GPVI), integrin, heat shock protein 47, and vitronectin.

Item 8. The method according to any one of items 5 to 7, wherein the sample solution includes plasma.

Item 9. The method according to any one of items 6 to 8, wherein the eluting agent is selected from the group consisting of NaCl, KCl, $MgCl_2$, $CaCl_2$, $Na_2SO_4$, NaBr, KBr, sodium acetate, tris hydrochloride, phosphate, a guanidine salt, arginine and a salt thereof, and urea.

Effects of Invention

In the invention, a chemically synthesized polypeptide is used as an adsorbent. Therefore, as compared with a native collagen or the like, the polypeptide has a high resistance to deterioration by a washing fluid and a high resistance to decomposition by protease to allow easy production and procurement due to a simple sequence repetition, and further allow dissolution of a matter of concern for use of an animal origin material. Moreover, a blood coagulation factor or a cell adhesion factor can be adsorbed on the adsorbent of the invention and desorbed from the adsorbent only by a change of concentration of a salt or urea. Therefore, cost can be suppressed, and degeneration of the blood coagulation factor or the cell adhesion factor can be prevented.

Accordingly, the invention provides a method for purifying the blood coagulation factor or the cell adhesion factor under mild conditions, according to simple procedures, and at a low cost and safely while having a high affinity with an object substance and a high resistance to deterioration.

DESCRIPTION OF EMBODIMENTS

In the invention, various amino acid residues are described by means of abbreviations as described below.

Ala: L-alanine residue;
Arg: L-arginine residue;
Asn: L-asparagine residue;
Asp: L-aspartyl residue;
Cys: L-cysteine residue;
Gln: L-glutamine residue;
Glu: L-glutamate residue;
Gly: glycine residue;
His: L-histidine residue;
Hyp: L-hydroxyproline residue;
Ile: L-isoleucine residue;
Leu: L-leucine residue;
Lys: L-lysine residue;
Met: L-methionine residue;
Phe: L-phenylalanine residue;
Pro: L-proline residue;
Sar: sarcosine residue;
Ser: L-serine residue;
Thr: L-threonine residue;
Trp: L-tryptophan residue;
Tyr: L-tyrosine residue; and
Val: L-valine residue.

In addition, an amino acid sequence of peptide chains herein is described by drawing an N-terminus of an amino acid residue on a left-hand side and a C-terminus thereof on a right-hand side in accordance with an ordinary procedure.

1. Adsorbent of the Invention

A polypeptide contained in the adsorbent of the invention has peptide fragments represented by formula (1) (hereinafter, described as polyPHG):

$$-(\text{Pro-Hyp-Gly}_n- \quad (1)$$

wherein Hyp represents 4Hyp, for example, and is preferably trans-4-hydroxy-L-proline.

Moreover, in formula (1), n as the number of repetition is an integer from 2 to 9,000. When n is in the range, the polypeptide can adsorb the blood coagulation factor, the cell adhesion factor or the like with a high affinity. Then, n is preferably in the range of approximately 5 to approximately 1,000, further preferably, in the range of approximately 10 to approximately 500 from a viewpoint of ligand stability by formation of a triple helical structure.

The polypeptide contained in the adsorbent of the invention can have the triple helical structure when n as the number of repetition is approximately 5 or more. The polypeptide does not necessarily have the triple helical structure, and may have a random coil structure in order cause adsorptive action with the blood coagulation factor, the cell adhesion factor or the like. However, if the polypeptide has the triple helical structure, stability as a ligand is improved, as described above. The polypeptide chains forming the triple helical structure may have a linear form or one or more branches. When the polypeptide chains have one or more branches, the triple helical structure may be formed in and after a branch point, and further the polypeptide chains may have one or more branches after the triple helical structure.

In addition, whether or not the polypeptide has the triple helical structure can be confirmed by measuring a circular dichroism spectrum for a polypeptide solution. Specifically, when a positive Cotton effect is shown in the range of approximately 220 to approximately 230 nanometers in the wavelength, and a negative Cotton effect is shown in the range of approximately 195 to approximately 205 nanometers in the wavelength, the polypeptide is considered to have the triple helical structure.

Moreover, the polypeptide chains contained in the adsorbent of the invention may be cross-linked with each other.

A weight average molecular weight of the polypeptide contained in the adsorbent of the invention is not particularly limited, but is preferably, in the range of approximately 570 to approximately 7,000,000, further preferably, in the range of approximately 2,850 to approximately 300,000 from a viewpoint of a high affinity with the blood coagulation factor or the cell adhesion factor, and stability of the triple helical structure.

Herein, the weight average molecular weight of the polypeptide can be measured, for example, according to a process by gel permeation chromatography using a column: Superdex 200 HR 10/30 (made by GE Healthcare Japan Corporation), at a flow rate: 0.5 mL/min, and using an eluate: 10 mM phosphate buffer (pH 7.4) containing 150 mM NaCl, and using GelFiltration LMW Calibration Kit and Gel Filtration HMW Calibration Kit (made by GE Healthcare Japan Corporation) as a molecular weight standard, as described in JP 2003-321500 A, or according to a process by gel permeation chromatography using a column: Superdex peptide PE 7.5/300 (made by GE Healthcare Japan Corporation), at a flow rate: 0.25 mL/min, and using an eluate: 10 mM phosphate buffer (pH 7.4) containing 150 mM NaCl, and using Gel Filtration LMW Calibration Kit (made by GE Healthcare Japan Corporation), human insulin and glycin as a molecular weight standard. As another method, the weight average molecular weight can be measured by HPLC gel permeation chromatography using a column: TSK-GEL6000 PW XL-CP 8.0×300 mm (made by Tosoh Corporation), a mobile phase: 20 mM $KH_2PO_4 \cdot H_3PO_4$ (pH 3.0): MeOH=8:2, at a column temperature of 40° C., and a flow rate of 0.5 mL/min, using 215 nanometers and a differential refractometer by a UV monitor for detection, and using a pullulan having a molecular weight of 50,000 to 1,600,000 (made by Showa Denko K. K) and dextran having a molecular weight of 11,900,000 (Polymer Standards Service GmbH) as a molecular weight standard. Moreover, the weight average molecular weight can be measured according to a Gel Permeation Chromatography with Multi-Angle Light Scattering (GPC-MALS) method by using DAWN HELEOS of Optolab rEX made by Wyatt Technology Corporation for a detector for the HPLC gel permeation chromatography. The weight average molecular weight of the polypeptide herein is expressed in terms of a value measured by the methods.

The polypeptide contained in the adsorbent of the invention may consist essentially of polyPHG, but may contain the amino acid residue, the peptide fragments or alkylene in addition to polyPHG within the range in which the stability of the triple helical structure and advantageous effects of the invention are not adversely affected.

Specific examples of the amino acid residue include at least one kind selected from the group consisting of Ala, Arg, Asn, Asp, Cys, Gln, Glu, Gly, His, Hyp, Ile, Leu, Lys, Met, Phe, Pro, Sar, Ser, Thr, Trp, Tyr, and Val. Specific examples of the peptide fragments include a peptide in which a plurality of one kind or two or more kinds of the amino acid residues are bonded. Alkylene may be either straight-chain alkylene or branch-chain alkylene, and is not particularly limited. Specific examples include alkylene having 1 to 18 carbons, preferably, alkylene having 2 to 12 carbons for practical purposes.

The polypeptide contained in the adsorbent of the invention has polyPHG, and the amino acid residue, the peptide fragments or alkylene other than polyPHG in the range of approximately 1:99 to approximately 100:0, preferably, in the range of approximately 10:90 to approximately 100:0 in terms of a weight ratio of polyPHG to the amino acid residue, the peptide fragments or alkylene other than polyPHG.

The polypeptide contained in the adsorbent of the invention has polyPHG, and the amino acid residue, the peptide fragments or alkylene other than polyPHG in the range of approximately 1:99 to approximately 100:0, preferably, in the range of approximately 10:90 to approximately 100:0 in terms of a weight ratio of polyPHG to the amino acid residue, the peptide fragments or alkylene other than polyPHG.

The polypeptide contained in the adsorbent of the invention may be a salt with an inorganic acid (hydrochloric acid, sulfuric acid or the like), an organic acid (acetic acid, lactic acid, maleic acid, oxalic acid, citric acid or the like), metal (sodium, potassium or the like) and an organic base (trimethylamine, triethylamine or the like), as long as adsorption of the blood coagulation factor or the cell adhesion factor is not adversely affected. A salt compound of the polypeptide contained in the adsorbent of the invention may be alone or in combination of two or more kinds.

The adsorbent of the invention may contain a substance other than the polypeptide having polyPHG within the range in which advantageous effects of the invention are not adversely affected. Other substances may be selected in consideration of storage stability, ease of handling, stability of activity, or the like, and are not particularly limited. Specific examples include a storage solvent as described later.

The polypeptide having polyPHG may be applied as obtained by any process. For example, the polypeptide having polyPHG can be preferably obtained by carrying out a condensation reaction using a peptide oligomer including amino acid that constitutes polyPHG obtained according to a known solid phase synthetic process or liquid phase synthetic process.

The condensation reaction of the peptide oligomer is ordinarily carried out in a solvent. The solvent may be used, if the solvent can (partially or wholly) dissolve or suspend the peptide oligomer applied as a raw material, and water or an organic solvent can be ordinarily used. Specific examples include water, amides (dimethylformamide, dimethylacetamide or hexamethylphosphoramide), sulfoxides (dimethylsulfoxide), a nitrogen-containing cyclic compound (N-methylpyrrolidone or pyridine), nitriles (acetonitrile), ethers (dioxane or tetrahydrofuran), alcohols (methyl alcohol, ethyl alcohol or propyl alcohol), and a mixed solvent of the solvents described above. Among the solvents, water, dimethylformamide or dimethylsulfoxide is preferably used.

Moreover, the condensation reaction of the peptide oligomer is preferably carried out in the presence of a dehydration agent (a dehydration-condensation agent or a condensation auxiliary). If the condensation reaction is allowed in the presence of the dehydration-condensation agent and the condensation auxiliary, the condensation reaction smoothly progresses without passing through complicated treatment in which deprotection and amino acid bonding are repeated while suppressing dimerization or cyclization.

The dehydration-condensation agent is not particularly limited, as long as dehydration condensation can be efficiently performed in the solvent. Specific examples include a carbodiimide condensation agent (diisopropylcarbodiimide (DIPC), 1-ethyl-3-(3-dimethylaminopropyl)-carbodiimide (EDC=WSCI), 1-ethyl-3-(3-dimethylaminopropyl)-carbodiimide hydrochloride (WSCI.HCl) or dicyclohexylcarbodiimide (DCC)), a fluorophosphate condensation agent (O-(7-azabenzotriazole-1-yl)-1,1,3,3-tetramethyluronium hexafluorophosphate, O-benzotriazole-1-yl-N,N,N,N'-tetramethyluronium hexafluorophosphate, benzotriazole-1-yl-oxy-tris-pyrrolidinophosphonium hexafluorophosphate, benzotriazole-1-yl-tris(dimethylamino)phosphonium hexafluorophosphate (BOP)) or diphenylphosphoryl azide (DPPA).

The dehydration-condensation agents can be used alone or in the form of a mixture in combination of two or more kinds. A preferred dehydration-condensation agent includes a carbodiimide condensation agent (1-ethyl-3-(3-dimethylaminopropyl)-carbodiimide or 1-ethyl-3-(3-dimethylaminopropyl)-carbodiimide hydrochloride, for example).

When a non-aqueous solvent containing no water is used, an amount of the dehydration-condensation agent used is ordinarily in the range of approximately 0.7 to approximately 5 mol, preferably, in the range of approximately 0.8 to approximately 2.5 mol, further preferably, in the range of approximately 0.9 to approximately 2.3 mol (approximately 1 to approximately 2 mol, for example), based on 1 mol of the total amount of the peptide fragments. In a solvent containing water (aqueous solvent), inactivation of the dehydration-condensation agent by water is caused. Therefore, an amount of the dehydration-condensation agent used is ordinarily in the range of approximately 2 to approximately 500 mol, preferably, in the range of approximately 5 to approximately 250 mol, further preferably, in the range of approximately 10 to approximately 125 mol, based on 1 mol of the total amount of the peptide fragments.

The condensation auxiliary is not particularly limited, as long as the condensation auxiliary promotes the condensation reaction. Specific examples include N-hydroxy polycarboxylic imides (N-hydroxy dicarboxylic imides such as N-hydroxysuccinimide (HONSu) and N-hydroxy-5-norbornene-2,3-dicarboxylic imides (HONB)), N-hydroxytriazoles (N-hydroxybenzotriazoles such as 1-hydroxybenzotriazole (HOBt)), triazines such as 3-hydroxy-4-oxo-3,4-dihydro-1,2,3-benzotriazine (HOObt) or 2-hydroxyimino-2-cyanoacetic acid ethyl ester.

The condensation auxiliaries can also be used alone or in combination of two or more kinds. A preferred condensation auxiliary includes N-hydroxy dicarboxylic imides (HONSu) and N-hydroxybenzotriazole or N-hydroxybenzotriazines (HOBt).

An amount of condensation auxiliary used is ordinarily in the range of approximately 0.5 to approximately 5 mol, preferably, in the range of approximately 0.7 to approximately 2 mol, further preferably, in the range of approximately 0.8 to approximately 1.5 mol, based on 1 mol of the total amount of the peptide fragments, regardless of kinds of solvents.

The dehydration-condensation agent and the condensation auxiliary are preferably suitably combined and used. Specific examples of combinations of the dehydration-condensation agent and the condensation auxiliary include DCC and HONSu (HOBt or HOOBt) or WSCI and HONSu (HOBt or HOOBt).

In the condensation reaction of the peptide oligomer, pH of a reaction solution may be adjusted, and ordinarily, is adjusted to vicinity of neutrality (pH is approximately 6 to approximately 8). Adjustment of pH can be ordinarily performed using an inorganic base (sodium hydroxide, potassium hydroxide, sodium carbonate, sodium hydrogencarbonate or the like), an organic base, an inorganic acid (hydrochloric acid or the like) or an organic acid.

Moreover, a base that is not involved in the condensation reaction may be added to the reaction solution. Specific examples of the bases that are not involved in the condensation reaction include tertiary amines such as trialkylamines including trimethylamine, triethylamine or diisopropylethylamine, or heterocyclic tertiary amines including N-methylmorpholine or pyridine. An amount of such a base used can be ordinarily selected from the range of approximately 1 to approximately 2 times of the total number of moles of the peptide oligomer.

A reagent used for the reaction remains in the polypeptide obtained as described above. The reagent affects adsorption capacity of the adsorbent of the invention to the blood coagulation factor or the cell adhesion factor, and therefore is preferably removed. Removal of the remaining reagent can be performed by using a known technique such as dialysis, a column process and ultrafiltration.

Moreover, a reaction solvent is preferably replaced by the storage solvent in view of stability of the polypeptide and ease of handling. Replacement from the reaction solvent to an object storage solvent can be performed by using the object solvent as a dialysis supplement buffer in the dialysis, or using the object storage solvent as a mobile phase in the column process.

The storage solvent is not particularly limited, if the storage solvent can suppress a change of physical properties and so forth of the polypeptide as the resultant effective component. Specific examples include water, a physiological salt solution, and a buffer having buffer capacity from weak acid to weak alkali. However, a substance that affects the blood coagulation factor or the cell adhesion factor is not preferably contained.

The adsorbent of the invention can adsorb the blood coagulation factor or the cell adhesion factor with a high affinity. Among the blood coagulation factors or the cell adhesion factors, a von Willebrand factor (hereinafter, described as vWF), fibronectin (hereinafter, described as FN), glycoprotein VI (hereinafter, described as GPVI), integrin, heat shock protein 47, and vitronectin have a high affinity with the adsorbent, and therefore are particularly preferred.

The adsorbent of the invention can purify or remove the blood coagulation factor or the cell adhesion factor from a protein mixture such as blood, or can purify a recombinant protein produced with a bacterial cell, yeast or the like. Therefore, the adsorbent can be suitably used for purification or production of an object blood coagulation factor or an object cell adhesion factor.

The adsorbent of the invention can be applied in an embodiment in which the adsorbent is immobilized on a solid phase carrier. A material of such a solid phase carrier is not particularly limited, and a known material such as a cellulose, polymer, silica or agarose material can be used. Moreover, a form thereof is not particularly limited, and includes beads, a plate and a fiber.

As for immobilization, the adsorbent of the invention is preferably immobilized on the solid phase carrier by a covalent bond from a viewpoint of preventing desorption of the adsorbent during operation. The immobilization by the covalent bond can be performed according to a generally known process in which a reactive group such as an ester group, an aldehyde group and an epoxy group is introduced onto a surface of the solid phase carrier, and a coupling reaction with an amino group or a hydroxy group of the polypeptide contained in the adsorbent of the invention is carried out on the surface of the solid phase carrier, for example. In addition, various commercial products are available as the solid phase carriers onto which surface the reactive group is introduced, and therefore can be suitably utilized. An amount of the polypeptide immobilized on the solid phase carrier can be arbitrarily set up, as long as advantageous effects of the invention are not adversely affected.

Such an immobilized solid phase carrier can be included in a protein purification kit, for example, and can be suitably used for a method for purifying the blood coagulation factor or the cell adhesion factor as described later.

2. A Purification Method of the Invention

The purification method of the invention includes an adsorption step for bringing a sample solution into contact with the adsorbent of the invention or the solid phase carrier on which the adsorbent of the invention is immobilized to adsorb the blood coagulation factor or the cell adhesion factor on the adsorbent. Moreover, according to a further embodiment, the method further includes an elution step for bringing an eluate containing an eluting agent into contact with the adsorbent or the solid phase carrier after the adsorption step to elute the blood coagulation factor or the cell adhesion factor.

In the purification method of the invention, the blood coagulation factor or the cell adhesion factor in the sample solution can be purified. In particular, among the blood coagulation factors or the cell adhesion factors, vWF, FN, GPVI, integrin, heat shock protein 47, and vitronectin can be preferably selected as a purification object.

The sample described above is not particularly limited. Specific examples include whole blood, plasma, a culture liquid for a cell, a cell extract, serum, a body fluid or a product of a recombination cell, particularly preferably, plasma. In the case of a living body origin sample such as whole blood or plasma, the method can be applied to any animal origin sample, preferably, a human origin sample.

The purification method of the invention can be applied to purification or removal of the blood coagulation factor or the cell adhesion factor from the protein mixture such as blood, or purification of a recombinant protein produced with a bacterial cell, yeast or the like. Therefore, the purification method can be suitably applied to purification or production of the object blood coagulation factor or the object cell adhesion factor.

In the following, each step of the purification method of the invention will be explained.

In the adsorption step in the purification method of the invention, the sample solution ordinarily contains approximately 0.01 to approximately 0.5 M of salt or urea. The reason is that the stability of the blood coagulation factor or the cell adhesion factor is adversely affected with a concentration lower than approximately 0.01 M, and the adsorption of the blood coagulation factor or the cell adhesion factor on the adsorbent is adversely affected with a concentration higher than approximately 0.5 M. In addition, specific examples of kinds of salts include NaCl, KCl, $MgCl_2$, $CaCl_2$, $Na_2SO_4$, NaBr, KBr, sodium acetate, tris hydrochloride, phosphate, a guanidine salt, arginine and a salt thereof. The kinds of salts are not particularly limited, and two or more kinds of salts, or a salt and urea may be combined and used. The sample can be adjusted by dilution with Tris-HCl, phosphate, acetate, carbonate, citric acid, and a publicly known buffer such as a Good's buffer, and pH thereof is adjusted in the range in which the stability of the blood coagulation factor or the cell adhesion factor is not adversely affected, for example, in the range of approximately 4 to approximately 9.

In the adsorption step, the blood coagulation factor or the cell adhesion factor is adsorbed on the adsorbent by bringing the sample solution into contact with the adsorbent of the invention. If the solid phase carrier in which the adsorbent of the invention is immobilized is used, an operation of adsorption can be easily performed. For example, the sample solution may be passed through a column in which such an immobilized carrier is packed. In the case, a rate or the number of times of passing the sample solution can be suitably adjusted such that the adsorption is sufficiently performed. Moreover, the sample solution is put in a vessel (the vessel per se may be the immobilized carrier) in which the immobilized carrier is put, and then the immobilized carrier may be recovered by removal of the sample solution, or the like after the vessel is left for a period of time sufficient for adsorption (with or without stirring of the solution).

After the adsorption step, when necessary, the adsorbent may be washed with the washing fluid, for example, a buffer solution containing approximately 0.01 to approximately 0.5 M of salt or urea. Thus, molecules nonspecifically adsorbed on the adsorbent or unabsorbed molecules may be eliminated.

Moreover, a temperature in the adsorption step is not particularly limited, but the adsorption is preferably performed at a temperature in the range of approximately 2° C. to approximately 37° C., further preferably, in the range of approximately 4° C. to approximately 25° C. from a viewpoint of preventing degeneration of the adsorbent or protein.

In the elution step in the purification method of the invention, the eluate to be used contains the eluting agent, and a concentration of the eluting agent is in the range of approximately 0.5 to approximately 1 M. The reason is that the blood coagulation factor or the cell adhesion factor is hardly desorbed from the adsorbent with a concentration lower than approximately 0.5 M, and elution efficiency plateaus, and also the stability of the blood coagulation factor or the cell adhesion factor is adversely affected with a concentration higher than approximately 1 M. Specific examples of kinds of eluting agents include NaCl, KCl, $MgCl_2$, $CaCl_2$, $Na_2SO_4$, NaBr, KBr, sodium acetate, tris hydrochloride, phosphate, a guanidine salt, arginine and a salt thereof, and urea. The kinds of eluting agents are not particularly limited, and two or more kinds of eluting agents may be combined and used. Moreover, pH of the eluate may be adjusted in the range in which the stability of the blood coagulation factor or the cell adhesion factor is not adversely affected, for example, in the range of approximately 4 to approximately 9.

In the purification method of the invention, the blood coagulation factor or the cell adhesion factor that is adsorbed on the adsorbent can be eluted and recovered by a simple means of increasing a concentration of salt or urea in the eluate, as compared with a concentration of the solution used in the adsorption step. The purification method allows purification under remarkably milder conditions, as compared with the affinity chromatography that has been applied so far, and has no fear of deteriorating the polypeptide having polyPHG to be the blood coagulation factor or the cell adhesion factor or the ligand. Moreover, a large amount of expensive reagent is not used. Therefore, efficiency is very high.

If the immobilized solid phase carrier is used, an operation in the elution step can also be easily performed in a manner similar to the adsorption step. More specifically, the eluate may be passed through a column in which the immobilized carrier after the adsorption step is packed. In the case, a rate or the number of times of passing the eluate can be suitably adjusted such that the elution is sufficiently performed. Moreover, the eluate may be put in a vessel (the vessel per se may be the immobilized carrier) in which the immobilized carrier after the adsorption step is put, and then the eluate may be recovered after the vessel is left for a period of time sufficient for elution (with or without stirring of the solution).

Moreover, a temperature in the elution step is not particularly limited, but the elution is preferably performed at a temperature in the range of approximately 4° C. to approximately 25° C.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

In the following, the invention will be explained in greater detail by way of Examples, but the invention is in no way limited to the Examples.

Immobilization of a Ligand

A polyPHG-containing polypeptide as an adsorbent of the invention, or collagen for comparison was immobilized on a gel carrier as an affinity ligand according to a known process.

Example 1

Cellufine Formyl (made by JNC Corporation) was washed with 50 mM of sodium carbonate, 4.3 g of washed gel obtained by suction filtration was put in a 200 mL Erlenmeyer flask, and further 16 g of aqueous solution of polyPHG-containing polypeptide having a concentration of at 0.5% by weight, 6.4 mL of 50 mM sodium carbonate and 9.6 mL of water were added therein, the resultant mixture was thoroughly mixed, and then shaken at 40° C. for 2 hours. Then, 0.7 mL of sodium borohydride 50 mg/mL aqueous solution was added, and the resultant mixture was further shaken at 40° C. for 2 hours. After completion of the reaction, a gel was recovered by suction filtration of reaction slurry. The gel was washed with 50 mM of sodium carbonate, a hydrochloric acid aqueous solution (pH 3) and pure water in order to remove an unreacted material and so forth remained in the gel, and a polyPHG immobilized gel was obtained by suction filtration.

An amount of polyPHG-containing polypeptide remained in a washing fluid was quantitatively determined, and an amount of immobilized polyPHG-containing polypeptide was calculated from a difference from an amount of polyPHG-containing polypeptide used for the reaction. An amount of polyPHG-containing polypeptide in the washing fluid was calculated by measuring a concentration from an absorbance at 210 nanometers.

The polyPHG-containing polypeptide used herein was a polypeptide consisting essentially of peptide fragments represented by formula (1), and having a weight average molecular weight of approximately 5,000,000. The polyPHG-containing polypeptide used herein will be used in and after Examples and Comparative Examples in a similar manner.

Comparative Example 1

Cellufine Formyl (made by JNC Corporation) was washed with 50 mM of sodium carbonate, 4.3 g of washed gel obtained by suction filtration was put in a 200 mL Erlenmeyer flask, and further 8 g of purified pig skin collagen 1% solution (made by Nippon Meat Packers, Inc.) and 24 mL of 50 mM sodium carbonate were added therein, the resultant mixture was thoroughly mixed, and then shaken at 40° C. for 2 hours. Then, 0.7 mL of sodium borohydride 50 mg/mL aqueous solution was added, and the resultant mixture was further shaken at 40° C. for 2 hours. After completion of the reaction, a gel was recovered by suction filtration of reaction slurry. The gel was washed with 50 mM of sodium carbonate, a hydrochloric acid aqueous solution (pH 3) and pure water in order to remove an unreacted material and so forth remained in the gel, and a collagen immobilized gel was obtained by suction filtration.

An amount of collagen remained in a washing fluid was quantitatively determined, and an amount of immobilized collagen was calculated from a difference from an amount of collagen used for the reaction. An amount of collagen in the washing fluid was calculated by measuring a concentration from an absorbance at 210 nanometers.

Example 2

Then, 2.7 g (dry weight) of Shodex BIOACT gel EPO series (made by Showa Denko K.K.) was weighed and added to 30 mL of polyPHG-containing polypeptide having a concentration of 0.25% by weight, and 50 mM sodium carbonate solution, and the resultant mixture was shaken at 40° C. overnight to allow reaction. After completion of the reaction, a gel was recovered by suction filtration of reaction slurry. The gel was washed with 50 mM of sodium carbonate, a hydrochloric acid aqueous solution (pH 3) and pure water in order to remove an unreacted material and so forth remained in the gel, and a polyPHG immobilized gel was obtained by suction filtration.

An amount of polyPHG-containing polypeptide remained in a washing fluid was quantitatively determined, and an amount of immobilized polyPHG-containing polypeptide was calculated from a difference from an amount of polyPHG-containing polypeptide used for the reaction. An amount of polyPHG-containing polypeptide in the washing fluid was calculated by measuring a concentration from an absorbance at 210 nanometers.

Example 3

A polyPHG immobilized gel was obtained in a manner similar to Example 2 except that a reaction temperature was changed to 4° C. from 40° C. in Example 2.

Comparative Example 2

Then, 2.7 g (dry weight) of Shodex BIOACT gel EPO series (made by Showa Denko K.K.) was weighed, and added to 30 mL of purified pig skin collagen solution diluted to 0.25% by weight (made by Nippon Meat Packers, Inc.), and 50 mM sodium carbonate solution, and the resultant mixture was shaken at 40° C. overnight to allow reaction. After completion of the reaction, a gel was recovered by suction filtration of reaction slurry. The gel was washed with 50 mM of sodium carbonate, a hydrochloric acid aqueous solution (pH 3) and pure water in order to remove an unreacted material and so forth remained in the gel, and a collagen immobilized gel was obtained by suction filtration.

An amount of collagen remained in a washing fluid was quantitatively determined, and an amount of immobilized collagen was calculated from a difference from an amount of collagen used for the reaction. An amount of collagen in the washing fluid was calculated by measuring a concentration from an absorbance at 210 nanometers.

Comparative Example 3

A collagen immobilized gel was obtained in a manner similar to Comparative Example 2 except that a reaction temperature was changed to 4° C. from 40° C. in Comparative Example 2.

Table 1 shows an amount of ligand immobilized on the gel carriers in Examples 1 to 3 and Comparative Examples 1 to 3.

TABLE 1

|  | Gel carrier | Ligand | Immobilized amount (mg/mL-gel) |
|---|---|---|---|
| Example 1 | Cellufine Formyl | PolyPHG | 6 |
| Comparative Example 1 |  | Collagen | 6 |
| Example 2 | Shodex BIOACT gel | PolyPHG | 12 |
| Example 3 | EPO series | PolyPHG | 13 |
| Comparative Example 2 |  | Collagen | 7 |
| Comparative Example 3 |  | Collagen | 10 |

Adsorption and Elution Experiment of a Plasma Component 1

Then, 1 mL of each of the immobilized gel carriers in Example 1 and Comparative Example 1, and 6 wt. % cellulose particles (made by JNC Corporation) as a raw material of the gel carrier was packed in a column made of polypropylene. A liquid of 5 mL or more of 100 mM Tris-HCl (pH 7.5) (hereinafter, described as TB) was passed to be equilibrated, and then 5 mL of Plasma, human (Sigma/P9523-5mL) as diluted by 10 times with TB was passed through the column (single time). Then, 5 mL of TB was passed through the column to wash away an unabsorbed plasma component (single time). A liquid from a column outlet was gathered and recovered as a pass-through and washing fluid. After completion of washing, 5 mL of TB containing 1 M NaCl was passed through the column (single time), and a liquid from the column outlet was recovered as an eluate. All of the operations were performed under room temperature (25° C.).

An amount of each of FN and vWF contained in the pass-through and washing fluid, and the eluate was measured by means of ELISA.

Table 2 shows the results of adsorption and elution of FN, and Table 3 shows the results of adsorption and elution of vWF.

The adsorbent of the invention could efficiently adsorb FN and vWF in the plasma, and adsorbed FN and vWF could be easily recovered by the eluate containing 1 M NaCl. In particular, an amount of vWF adsorbed on the adsorbent of the invention was higher, as compared with the collagen, and the adsorbent of the invention was found to have a high affinity with vWF. Moreover, in particular, an amount of FN adsorbed on the adsorbent was comparable, as compared with the collagen. However, FN could be easily recovered by only a simple elution operation of increasing a salt concentration.

TABLE 2

Results of adsorption and elution of FN

| Gel | Pass-through and washing fluid (μg) | Adsorption amount (μg) | Elution amount (μg) | Recovery ratio (%) |
|---|---|---|---|---|
| 6 wt. % cellulose particles | 246 | 0 | 0 | — |
| Example 1 | 8 | 220 | 226 | 102.7 |
| Comparative Example 1 | 10 | 218 | 75 | 34.4 |

TABLE 3

Results of adsorption and elution of vWF

| Gel | Pass-through and washing fluid (mU) | Adsorption amount (mU) | Elution amount (mU) | Recovery ratio (%) |
|---|---|---|---|---|
| 6 wt. % cellulose particles | 880 | 0 | 0 | — |
| Example 1 | 190 | 554 | 426 | 76.9 |
| Comparative Example 1 | 573 | 171 | 103 | 60.2 |

Adsorption and Elution Experiment of a Plasma Component 2

The adsorption elution experiment was performed in a manner similar to the adsorption elution experiment 1 except that an eluate was changed to TB containing 0.7 M arginine and 0.3 M NaCl. An amount of FN contained in each of a pass-through and washing fluid and an eluate was measured by means of ELISA.

Table 4 shows the results of adsorption and elution of FN.

From Table 2 and Table 4, an amount of FN adsorbed was found to be comparable between Example 1 and Comparative Example 1. However, the adsorbent of the invention was found to be more advantageous in the elution conditions. More specifically, only 34.4% of FN adsorbed could be eluted under the conditions of 1M NaCl in Comparative Example 1 (collagen), but 99.2% could be eluted under the conditions of 0.7 M arginine and 0.3 M NaCl. Whereas, 100% of FN adsorbed could be recovered under mild conditions of 1 M NaCl even without using the arginine.

TABLE 4

Results of adsorption and elution of FN

| Gel | Pass-through and washing fluid (μg) | Adsorption amount (μg) | Elution amount (μg) | Recovery ratio (%) |
|---|---|---|---|---|
| Example 1 | 2 | 256 | 256 | 100.0 |
| Comparative Example 1 | 3 | 254 | 252 | 99.2 |

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

Industrial Applicability

According to the invention, a blood coagulation factor or a cell adhesion factor can be recovered or removed even from a complicated protein mixture such as plasma under mild conditions, according to simple procedures, and at a low cost and safely while having a high affinity with an object substance and a high resistance to deterioration. The invention can be applied to purification of the blood coagulation factor or the cell adhesion factor and production of a biomedicine using the blood coagulation factor or the cell adhesion factor, and therefore is industrially very useful.

What is claimed is:

1. A method for purifying a blood coagulation factor or a cell adhesion factor in a sample solution, comprising:
   i) an adsorption step for bringing the sample solution into contact with an adsorbent for a blood coagulation factor or a cell adhesion factor comprising a polypeptide having peptide fragments represented by formula (1) to adsorb the blood coagulation factor or the cell adhesion factor on the adsorbent, wherein the formula (1) is -(Pro-Hyp-Gly)$_n$-, wherein n is an integer from 2 to 9,000; and
   ii) an elution step for bringing an eluting agent-containing eluate into contact with the adsorbent after the adsorption step to elute the blood coagulation factor or the cell adhesion factor.

2. The method according to claim 1, wherein the blood coagulation factor or the cell adhesion factor is selected from the group consisting of a von Willebrand factor, fibronectin, glycoprotein VI (GPVI), integrin, heat shock protein 47, and vitronectin.

3. The method according to claim 1, wherein the sample solution comprises plasma.

4. The method according to claim 1, wherein the eluting agent is selected from the group consisting of NaCl, KCl, MgCl$_2$, CaCl$_2$, Na$_2$SO$_4$, NaBr, KBr, sodium acetate, tris hydrochloride, phosphate, a guanidine salt, arginine and a salt thereof, and urea.

5. The method according to claim 1, wherein a weight average molecular weight of the polypeptide is in the range of 570 to 7,000,000.

* * * * *